United States Patent [19]

Kovach

[11] Patent Number: 4,489,213

[45] Date of Patent: Dec. 18, 1984

[54] ALUMINA CATALYST FOR ALKYLATING AROMATICS WITH OLEFINS

[75] Inventor: Stephen M. Kovach, Ashland, Ky.

[73] Assignee: Ashland Oil, Inc., Ashland, Ky.

[21] Appl. No.: 278,248

[22] Filed: Jun. 29, 1981

Related U.S. Application Data

[60] Continuation-in-part of Ser. No. 180,965, Aug. 25, 1980, Pat. No. 4,285,835, which is a continuation-in-part of Ser. No. 55,221, Jul. 5, 1979, abandoned, which is a division of Ser. No. 860,503, Dec. 14, 1977, abandoned.

[51] Int. Cl.$^3$ .............................................. C07C 2/68
[52] U.S. Cl. .................................................... 585/467
[58] Field of Search ......................... 585/467; 252/432

[56] References Cited

U.S. PATENT DOCUMENTS

| | | | |
|---|---|---|---|
| 2,542,190 | 2/1951 | Gorin et al. | 585/467 |
| 2,972,642 | 2/1961 | Pfefferle et al. | 585/467 |
| 4,219,690 | 8/1980 | Kovach | 585/467 |

*Primary Examiner*—Curtis R. Davis

[57] ABSTRACT

Mixtures of aromatic and olefinic hydrocarbons are contacted in the presence of a catalyst under appropriate pressure, temperature and space velocity to effect alkylation of the aromatic hydrocarbon. The catalyst is alumina containing boria and an oxide of a metal from Group IVA (tin and lead) or Group VIIB (manganese).

10 Claims, No Drawings

ALUMINA CATALYST FOR ALKYLATING AROMATICS WITH OLEFINS

This application is continuation-in-part of my copending application Ser. No. 180,965, filed Aug. 25, 1980, now U.S. Pat. No. 4,285,835, which in turn is a continuation-in-part of my application Ser. No. 055,221, filed July 5, 1979, now abandoned, which is in turn a division of application Ser. No. 860,503, filed Dec. 14, 1977, and now abandoned.

DISCUSSION OF THE PRIOR ART

It is well known that aromatic compounds can be alkylated with olefins over Friedel-Crafts catalysts or over solid-oxide type catalysts. Use of Friedel-Crafts catalysts, (for example, aluminum chloride), is accompanied by high catalyst consumption due to the formation of a catalyst-oil sludge layer. These catalysts also require special equipment to combat their corrosive nature. The solid-oxide catalysts, e.g., silica-alumina or phosphoric acid on kieselguhr, effect high conversions in olefin-aromatic alkylations but lose activity due to the deposition of carbonaceous material on the catalyst. Consequently, high temperature regeneration is required and some catalysts are non-regenerable. The more common catalysts now used for the alkylation of aromatics yield alkylate products with a low ratio of para to meta compounds.

An object of this invention is to provide an alkylation catalyst which can be used under conditions wherein the aromatic material is in a liquid phase. Another object of this invention is to make available a catalyst for alkylation wherein the ratio of para to meta compounds in the resulting alkylated aromatic product is improved. Still another object is to provide an alkylation catalyst which can be regenerated easily.

SUMMARY OF THE INVENTION

Briefly stated, this invention comprises, in one aspect, a process for alkylating aromatic compounds with olefinic compounds comprising contacting the aromatic hydrocarbon with an olefinic compound in the presence of a catalyst of alumina containing boria and one or more metals selected from Group IVA (tin and lead), or VIIB (manganese) in the oxide form, under conditions of temperature, pressure and space velocity which effectively accomplish alkylation. In another aspect, this invention comprises the catalyst made up of alumina containing a boria and one or more metals selected from Group IVA (tin and lead), or VIIB (manganese) in the oxide form deposited thereon.

DESCRIPTION OF THE INVENTION

As stated above, the catalyst utilized in this invention is of alumina having deposited thereon boria and tin, lead, manganese or mixtures thereof in the oxide form. Preferably, the catalyst utilized in this invention is of alumina having deposited thereon boria and tin or lead or a mixture of tin and lead or a mixture of tin, lead and manganese in the oxide form. The alumina preferably is a high area alumina having a boehmite, bayerite, beta, or eta crystalline form.

The catalyst is prepared by techniques well known in the art. One may employ extrudates or pellets for impregnation, or powders followed by pelletization or extrusion to yield the finished catalyst. The boria and metal oxide are added by the use of water soluble salts, such as nitrates, sulfates, halides, acetates, etc. Well-known procedures for drying and calcining the catalyst may also be employed, such as vacuum drying and calcination in oxidative or neutral atmospheres. Calcination should be conducted at temperatures between about 450° and 550° C. The concentration of boria, ($B_2O_3$), in the finished catalyst should be from about 0.5 to about 15% by weight and preferably from about 1 to about 10 by weight. The total concentration of the metal or metals (in elemental form) should be between about 0.1 and about 4.0% by weight.

Aromatic hydrocarbons which can be alkylated by the process of this invention are those having at least one replaceable hydrogen such as benzene, toluene, xylene and naphthalene.

The preferred olefinic alkylating stock is one having 2–12 carbon atoms per molecule such as ethylene, propylene, butylene and dodecylene, and mixtures thereof.

To carry out the invention, a mixture of selected aromatic and olefinic hydrocarbons are contacted with the catalyst at desired operating conditions. Operating conditions employed in the process of the present invention are critical and will be dependent, at least in part, on the specific alkylation reaction being affected. Such conditions as temperature, pressure, space velocity and molar ratio of the reactants and the presence of inert diluents will have important effects on the process. Generally, an operating pressure of between about 100 and about 1000 psig, a temperature of between about 25° and about 150° C., a liquid-hourly-space velocity of between about 0.1 and about 10, a molar ratio of aromatics to olefins of between about 1:1 and about 20:1 can be used. More preferred conditions are about 100 to about 1000 psig, about 35° to about 150° C., a LHSV of about 1:1 to about 10:1 and a molar ratio of aromatics to olefin of about 2:1 and about 10:1. Preferred diluents are the paraffins and the naphthenes.

EXAMPLE 1

An aqueous solution of boric acid, $H_3BO_3$ and tin sulfate was prepared in a weight percent concentration of 11% $H_3BO_3$ and 5.7% tin sulfate. Catalyst prepared from this solution is designated as A in Table 1. A predetermined weight of alumina was then saturated with each of the solutions. Each portion of saturated alumina was dried and calcined at a temperature of 500° C. for 16 hours.

In laboratory tests, a mixture of toluene and propylene in a ratio of 6 moles toluene to 1 mole of propylene was passed over each of the catalysts at a pressure of 500 psig at temperatures of 25° to 125° C. and at the liquid-hourly-space velocities shown in Table I.

TABLE I

| Run | A | A | A | A | A | B | B |
|---|---|---|---|---|---|---|---|
| Catalyst | | | | | | | |
| Weight % of boria in catalyst | 10% | 10% | 10% | 10% | 10% | 10% | 10% |
| Weight % of metal in oxide form on catalyst | 2% tin | 2% tin | 2% tin | 4% tin | 4% tin | 4% Mn | 2% Mn |

TABLE I-continued

| Run | A | A | A | A | A | B | B |
|---|---|---|---|---|---|---|---|
| Operating Conditions | | | | | | | |
| Temperature - °C. | 32 | 116 | 127 | 54 | 127 | 24 | 60 |
| Pressure - psig | 500 | 500 | 500 | 500 | 500 | 500 | 500 |
| LHSV | 1 | 1 | 1 | 1 | 2 | 1 | 1 |
| Product distribution by boiling Point | | | | | | | |
| Less than Toluene | 1.1 | 0 | 0 | 0.8 | 0 | 1.2 | 1.6 |
| Toluene | 92.9 | 81.8 | 82.8 | 94.9 | 85.8 | 98.2 | 96.3 |
| m-cymeme | 0.7 | 1.8 | 1.8 | 0.5 | 1.8 | 0.1 | 0.2 |
| p-cymene | 2.5 | 7.1 | 6.4 | 1.8 | 6.1 | 0.3 | 1.1 |
| o-cymene | 2.2 | 6.0 | 5.8 | 1.5 | 5.0 | 0.2 | 0.8 |
| Greater than cymene | 0.6 | 3.3 | 3.2 | 0.5 | 1.3 | — | — |
| Weight % of Propylene Converted | | | | | | | |
| mono-alkylation | 24 | 67 | 63 | 17 | 58 | 3 | 9 |
| di-alkylation | 4 | 22 | 22 | 3 | 9 | 0 | 0 |
| polymerization | 16 | 0 | 0 | 11 | 0 | 17 | 23 |
| unconverted | 56 | 11 | 15 | 69 | 33 | 80 | 68 |
| Cymene distribution | | | | | | | |
| o- | 41 | 40 | 41 | 40 | 39 | 33 | 38 |
| m- | 13 | 12 | 13 | 13 | 14 | 17 | 10 |
| p- | 46 | 48 | 46 | 47 | 47 | 50 | 52 |
| ratio of para to meta | 78:22 | 80:20 | 78:22 | 78:22 | 77:23 | 75:25 | 84:16 |

An unexpected feature of this new catalyst-catalyst system is the isomer distribution of the product obtained. The presently used Friedel-Crafts catalyst and the more common solid oxide catalyst, when used to alkylate aromatics with olefins, yields product high in the meta isomer and low in the ortho and para isomer. For example, in the publication, "Organic Reactions," Volume III, John Wiley and Sons, Inc., page 46, the alkylation of toluene with n-butyl or t-butyl chloride with aluminum or iron chloride catalysts in a mole ratio of 5.6 to 1 is shown to yield a ratio of para to meta butyltoluene of 38:62 and 33:67. The catalysts of this invention yield products with the improved isomer distribution, namely, the produce is higher in ortho and para compounds and lower in the meta compounds, as indicated in Table I.

The catalyst of this invention is easily regenerated when it becomes fouled or spent. Because of the low temperatures of the alkylation process, deactivation occurs not by the deposition of carbon on the catalyst pores but by the plugging of the catalyst pores with heavy polymeric material. The catalyst is easily regenerated or restored by washing it with a paraffinic, naphthenic, or aromatic solvents. If a more strenuous regeneration is required, the catalyst can be reactivated by heating it to a temperature of between about 150° and about 370° C., in the presence of hydrogen or an inert gas such as nitrogen. This high temperature treatment will drive off the heavy polymeric material leaving only a small amount of carbon deposited on the catalyst surfaces.

When reference is made herein to groupings under the Periodic System of the elements, the particular groupings are as set forth in the Periodic Chart of the Elements in "The Merck Index," Ninth Edition, Merck & Co., Inc., 1976.

I claim:

1. A method for enhancing formation of para-isomers comprising alkylating an aromatic compound having at least one replaceable hydrogen with an olefinic hydrocarbon having between 2 and 12 carbon atoms per molecule comprising contacting said aromatic compound with said olefin in the presence of a catalytic amount of a catalyst comprising:
   (a) between about 0.1 and about 4% by weight of the oxide of a metal selected from the group consisting of tin, lead, mixtures of tin and lead and mixtures of tin, lead and manganese and;
   (b) between about 0.5 and 15% by weight of boria, both impregnated on an alumina support.

2. The method of claim 1 wherein the metal is selected from the group of tin, lead or mixtures thereof.

3. The method of claims 1, or 2, wherein the weight percent of boria, $B_2O_3$, is between about 1 and about 10.

4. The method of claims 1, or 2, wherein said aromatic hydrocarbon is selected from the group consisting of benzene, toluene, xylene, naphthalene, and mixtures thereof.

5. The method of claim 4 wherein said olefin is ethylene.

6. The method of claim 4 wherein said olefin is propylene.

7. The method of claim 4 wherein said olefin is butylene.

8. The method of claim 1, or 2, wherein said contacting is conducted at a pressure of between about 100 and about 1000 psig., a temperature of between about 25° and about 150° C., and a liquid-hourly-space velocity of between about 0.1 and about 10.

9. The method of claim 8 wherein the molar ratio of aromatics to olefin is about 1:1 to about 20:1.

10. The method of claim 8 wherein the temperature is about 35° to about 150° C.; the liquid-hourly-space velocity is about 1:1 to about 10:1 and the molar ratio of aromatics to olefin is about 2:1 to about 10:1.

* * * * *